(12) United States Patent
Niwa et al.

(10) Patent No.: US 9,176,655 B2
(45) Date of Patent: Nov. 3, 2015

(54) MEDICAL IMAGE OBSERVATION APPARATUS

(75) Inventors: Kenichi Niwa, Otawara (JP); Kenji Matsue, Nasushiobara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 437 days.

(21) Appl. No.: 13/366,872

(22) Filed: Feb. 6, 2012

(65) Prior Publication Data

US 2013/0141462 A1 Jun. 6, 2013

Related U.S. Application Data

(63) Continuation of application No. PCT/JP2011/077939, filed on Dec. 2, 2011.

(51) Int. Cl.
G09G 5/00 (2006.01)
G06F 3/0485 (2013.01)
G06F 19/00 (2011.01)

(52) U.S. Cl.
CPC ............ *G06F 3/0485* (2013.01); *G06F 19/321* (2013.01); *G06F 19/3406* (2013.01)

(58) Field of Classification Search
CPC ............ G09G 5/00; A61B 5/00; G06F 3/048; G06Q 50/24; G06Q 50/00
USPC .......................................... 715/784; 345/634
See application file for complete search history.

(56) References Cited

U.S. PATENT DOCUMENTS

| 6,976,231 | B1* | 12/2005 | Funahashi | 715/853 |
|---|---|---|---|---|
| 8,042,063 | B1 | 10/2011 | Lin-Hendel | |
| 2002/0101436 | A1* | 8/2002 | Shastri et al. | 345/619 |
| 2005/0259116 | A1* | 11/2005 | Araoka | 345/619 |
| 2010/0002013 | A1* | 1/2010 | Kagaya | 345/619 |
| 2010/0281371 | A1* | 11/2010 | Warner et al. | 715/720 |
| 2011/0069017 | A1* | 3/2011 | Victor | 345/173 |

(Continued)

FOREIGN PATENT DOCUMENTS

| CN | 1702645 A | 11/2005 |
|---|---|---|
| CN | 101388029 A | 3/2009 |

(Continued)

OTHER PUBLICATIONS

International Preliminary Report on Patentability and Written Opinion issued Jun. 12, 2014 in PCT/JP2011/077939 (submitting English language translation only).

(Continued)

*Primary Examiner* — Tadeese Hailu
*Assistant Examiner* — Alvaro R Calderon, IV
(74) *Attorney, Agent, or Firm* — Oblon, McClelland, Maier & Neustadt, L.L.P.

(57) ABSTRACT

According to one embodiment, a medical image observation apparatus includes a data receiver, a display, and a controller. The controller controls the display to array medical images for each of groups, the medical images being classified into the groups in accordance with at least one of a type of medical image generation apparatus, an imaging condition, an image generation method, an imaging position, an instruction and a setting by an operator, and an imaging date/time, to display medical images corresponding to at least two of the groups, and to scroll the medical images arrayed on a display screen on a group basis based on a scroll instruction of the operator.

12 Claims, 12 Drawing Sheets

(56) References Cited

U.S. PATENT DOCUMENTS

| | | | |
|---|---|---|---|
| 2011/0187751 A1* | 8/2011 | Oyama | 345/666 |
| 2011/0240872 A1* | 10/2011 | Sawada et al. | 250/393 |
| 2012/0036455 A1* | 2/2012 | Holt et al. | 715/753 |
| 2012/0042277 A1* | 2/2012 | Lin-Hendel | 715/784 |
| 2012/0066638 A1* | 3/2012 | Ohri | 715/784 |
| 2013/0036357 A1* | 2/2013 | Hendrickson | 715/728 |

FOREIGN PATENT DOCUMENTS

| | | |
|---|---|---|
| CN | 101751162 A | 6/2010 |
| CN | 102053786 A | 5/2011 |
| CN | 102200745 A | 9/2011 |
| EP | 1 229 459 A2 | 8/2002 |
| JP | 4-188369 | 7/1992 |
| JP | 7-85248 | 3/1995 |
| JP | 8-294485 | 11/1996 |
| JP | 2002-259006 A | 9/2002 |
| JP | 2003-108976 A | 4/2003 |
| JP | 2003-116838 | 4/2003 |
| JP | 2004-24861 A | 1/2004 |
| JP | 2005-301889 A | 10/2005 |
| JP | 2005-334634 A | 12/2005 |
| JP | 2007-260061 A | 10/2007 |
| JP | 2008-289916 | 12/2008 |
| JP | 2009-5906 | 1/2009 |
| JP | 2010-182018 A | 8/2010 |
| JP | 2011-41585 A | 3/2011 |

OTHER PUBLICATIONS

Japanese Office Action issued Aug. 5, 2014, in Japan Patent Application No. 2010-130328 (with English translation).

Combined Chinese Office Action and Search Report issued on Jul. 18, 2014, in Patent Application No. 201180003248.8 With English translation.

International Search Report mailed on Dec. 2, 2011, issued for international Application No. PCT/JP2011/077939 filed Dec. 2, 2011 (with English translation of Categories).

International Written Opinion mailed on Dec. 27, 2011 for International Application No. PCT/JP2011/077939 filed Dec. 2, 2011.

* cited by examiner

Additional information of medical image 512

| | | | | |
|---|---|---|---|---|
| No display | First image of group 1 of day examination (CT) | 10th image of group 2 of day examination (CT) | Middle image of group 3 of day examination (CT) | No display |
| Middle image of group 4 of day examination (MR) | Middle image of group 4 of past examination (CT) | Middle image of group 5 of day examination (CT) | Middle image of group 5 of past examination (CT) | Middle image of group 5 of day examination (CT) |
| First image of group 1 of day examination (MR) | No display | Middle image of group 2 of day examination (MR) | Middle image of group 2 of past examination (MR) | No display |
| Middle image of group 3 of day examination (MR) | Middle image of group 3 of past examination (MR) | Middle image of group 4 of day examination (MR) | Middle image of group 4 of past examination (MR) | Middle image of group 5 of day examination (MR) |
| Middle image of group 6 of past examination (MR) | Middle image of group 6 of day examination (MR) | Middle image of group 7 of day examination (MR) | Middle image of group 8 of day examination (MR) | No display |
| No display | No display | No display | No display | No display |
| No display | No display | No display | No display | No display |

F I G. 6

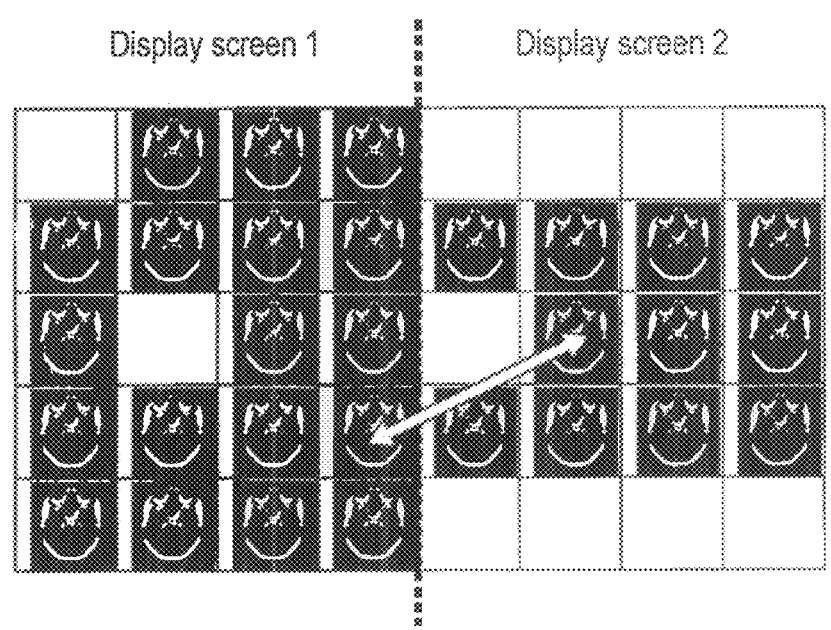
F I G. 7

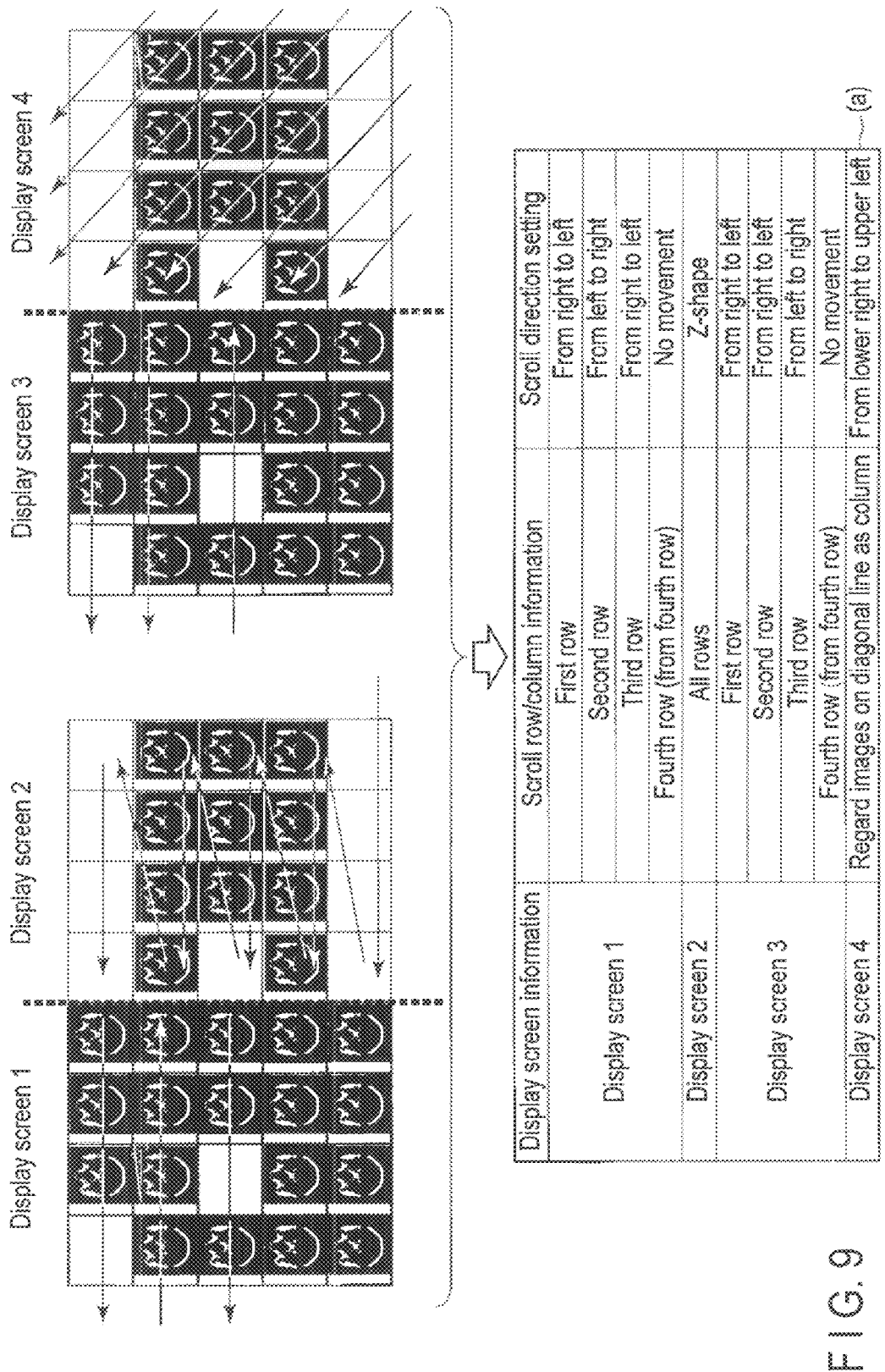
F I G. 9

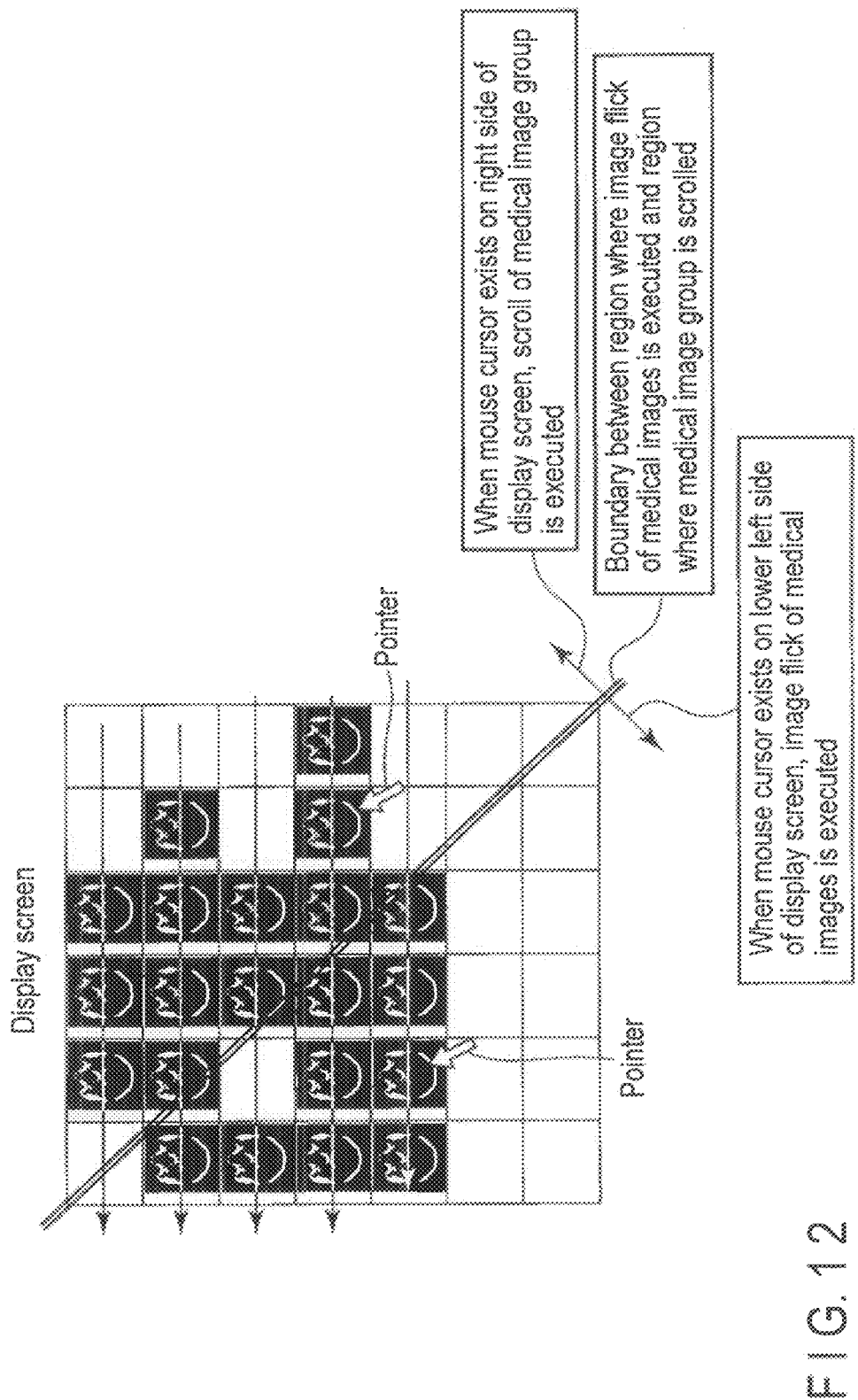
F I G. 12 ions to the embodiment, in which, for example, when the pointer is
MEDICAL IMAGE OBSERVATION APPARATUS

CROSS REFERENCE TO RELATED APPLICATIONS

This application is a Continuation Application of PCT Application No. PCT/JP2011/077939, filed Dec. 2, 2011, the entire contents of which are incorporated herein by reference.

FIELD

Embodiments described herein relate generally to a medical image observation apparatus.

BACKGROUND

A medical image observation apparatus conventionally displays a plurality of medical images to be interpreted in a preset place of a display screen on the series basis. For example, the display regions of the medical images to be interpreted are assigned to the display screen in accordance with the number of series selected by the interpretation doctor (for example, FIGS. 13 and 14).

However, the number of series displayed on the display screen is limited by the size of the display screen or the size of a medical image desired by the interpretation doctor. Hence, the medical image observation apparatus cannot display a medical image needed by the interpretation doctor.

BRIEF DESCRIPTION OF THE DRAWINGS

FIG. 6 is a view showing an example of a plurality of medical images arrayed on the display screen divided into a display region and a non-display region according to the embodiment in which the solid line indicates the display region, and the dotted line indicates the non-display region.

FIG. 7 is a view showing an example in which a medical image on display screen 1 and a medical image on display screen 2 are replaced with each other according to the embodiment.

FIG. 9 is a view showing an example in which some of medical images arrayed on a plurality of display screens are scrolled on the display screens on the group basis in accordance with a scroll instruction of an operator for each display screen according to the embodiment.

FIG. 12 is a view showing an example of the boundary between an area where a medical image replacement instruction is executed and an area where a medical image group scroll instruction is executed based on the position of a pointer on the display screen divided into two areas according to the embodiment, in which, for example, when the pointer is located on a medical image, or a series is selected (active), image flick is executed, or scroll may be executed by operating a wheel while pressing a shift (SHIFT) key, and image flick may be executed by operating the wheel without pressing the shift key.

DETAILED DESCRIPTION

Figure 1:
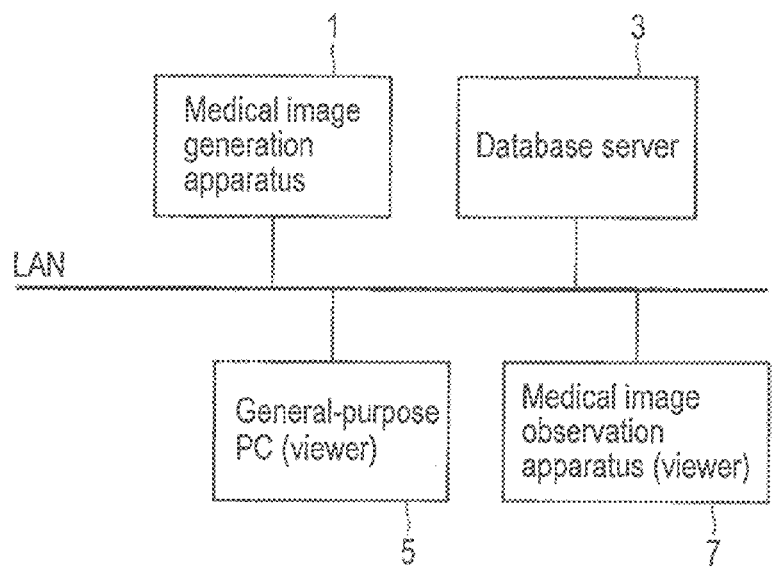
FIG. 1 is a block diagram showing an example of a system arrangement including a medical image observation apparatus according to an embodiment.

In general, according to one embodiment, a medical image observation apparatus includes a data receiver, a display, and a controller.

The data receiver is configured to receive a plurality of medical image data. The display configured to display medical images based on the plurality of medical image data received by the data receiver. The controller is configured to execute control to display the medical images on a display screen of the display.

The controller executes control to array the medical images for each of a plurality of groups, the medical images being classified into the groups in accordance with at least one of a type of medical image generation apparatus that has generated the medical image data, an imaging condition, an image generation method, an imaging position, an instruction of an operator, a setting by the operator, and an imaging date/time.

The controller executes control to display, on the display screen, a plurality of medical images corresponding to at least two of the groups.

The controller executes control to scroll the medical images arrayed on the display screen on a group basis based on a scroll instruction of the operator.

A medical image observation apparatus according to an embodiment will now be described with reference to the accompanying drawings. The medical image observation apparatus according to this embodiment is used to, for example, display two slice images concerning a single scan part of a single object parallelly on a screen and comparatively interpret them. Note that the same reference numerals in the following description denote constituent elements having almost the same functions and arrangements, and a repetitive description will be made only when necessary.

(Embodiment)

This embodiment will be described below with reference to the accompanying drawings.

FIG. 1 is a block diagram showing an example of a system configuration including a medical image observation apparatus according to this embodiment.

The system including a medical image observation apparatus includes a medical image generation apparatus 1, a database server 3, a general-purpose PC (Personal Computer) 5 serving as a viewer, and a medical image observation apparatus 7. Note that an image processing apparatus (not shown) may be connected via a local area network (to be referred to as a LAN hereinafter). The image processing apparatus performs image processing such as rendering processing for the data of a plurality of medical images generated by the medical image generation apparatus 1, thereby generating three-dimensional image data or multi-planar reconstructed image data.

The medical image generation apparatus 1 generates medical image data by imaging the inside of an object. The medical image generation apparatus 1 is, for example, an ultrasonic diagnostic apparatus that images the inside of an object by transmitting/receiving ultrasonic waves, an X-ray diagnostic apparatus or X-ray computed tomography apparatus (to be referred to as an X-ray CT (Computed Tomography) apparatus hereinafter) that images the inside of an object by X-ray exposure, or a magnetic resonance imaging apparatus (to be referred to as MR (Magnetic Resonance Imaging) hereinafter) that images the inside of an object by generating magnetic fields. The medical image generation apparatus 1 comprises a computer having a communication function and can perform data communication via the LAN.

The medical image generation apparatus 1 outputs medical image data including additional information to the database server 3. The additional information includes examination date/time information, a patient ID (IDentifier), an examination ID, a series ID, an image ID that is a number unique to a medical image, and image attribute information based on the DICOM (Digital Imaging and Communications in Medicine) standard. The pieces of information such as the patient ID, the examination ID, the series ID, the image ID, and the image attribute information are standardized in accordance with the DICOM standard. The patient ID is information to be used to specify an imaged object. The examination ID is information to be used to specify the examination contents. The series ID is information to be used to classify a plurality of generated medical images and includes an imaged part of an object, an image generation time, a slice thickness, an image generation method, a condition and position of imaging of an object, and the presence/absence of a contrast medium. The image generation method is, for example, a method of reconstructing a medical image based on projection data or signal data acquired by the medical image generation apparatus 1.

When a plurality of examinations are carried out on an object, a plurality of medical image data generated by the examinations are added with examination IDs representing the examinations and classified for each examination. When an examination includes a plurality of series because of, for example, imaging of a plurality of parts, a plurality of medical image data generated for each series are added with series IDs representing the series and classified for each series. That is, a plurality of medical images data with a given patient ID is classified by examination ID for each examination. In each examination, the medical image data are further classified by series ID for each series. The image attribute information is information to be used to specify a medical image type. The image attribute information includes, for example, a modality name, a modality manufacturer, an apparatus serial number, and information to be used to specify the examination part of an object. Note that although the additional information has been described above based on the DICOM standard, any other standard may be applied.

The database server 3 includes a plurality of hard disk drives (to be referred to as HDDs hereinafter) or NASes (Network Attached Storages) to store a plurality of medical images. The database server 3 receives, via the LAN, medical image data generated by the medical image generation apparatus 1 and added with additional information and stores them. The database server 3 receives, via the LAN, medical images added with annotations by the medical image observation apparatus 7 and stores them. The annotation is additional information added to a medical image and includes, for example, a marker added to a position of interest of a medical image, a character string representing the findings of a medical image, and a comment added to a medical image.

The general-purpose PC 5 serving as a viewer and the medical image observation apparatus 7 display, based on an instruction from an operator, a plurality of medical image data stored in the database server 3.

Figure 2:
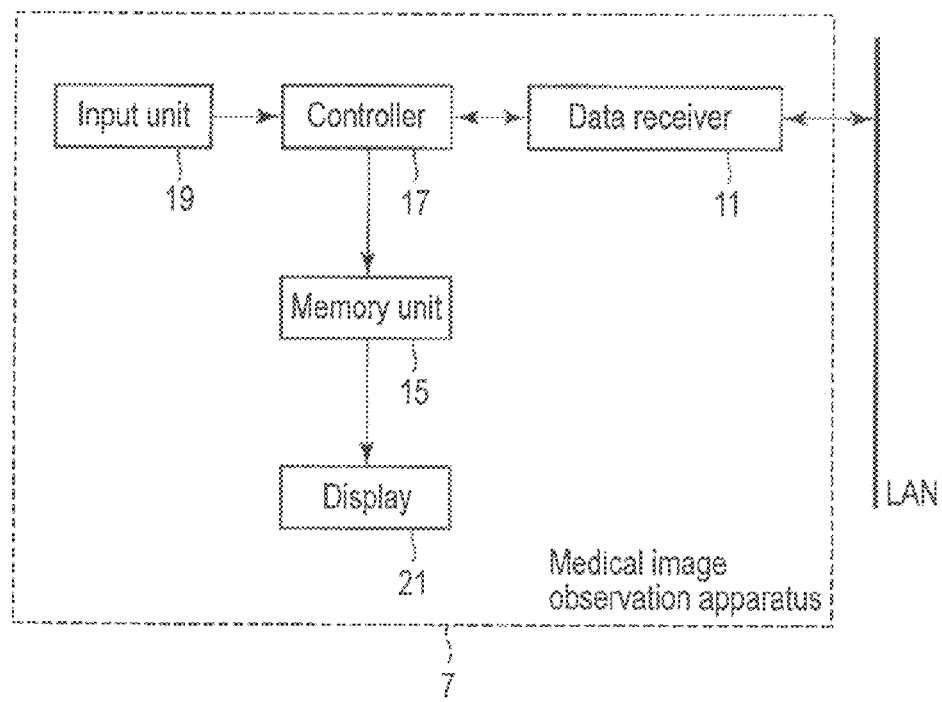
FIG. 2 is a block diagram showing an example of the block arrangement of the medical image observation apparatus according to the embodiment.

FIG. 2 is a block diagram showing an example of the block arrangement of the medical image observation apparatus 7 or the general-purpose PC 5 serving as a viewer according to the embodiment. The medical image observation apparatus 7 will be exemplified below as a viewer. The medical image observation apparatus 7 includes a data receiver 11, a memory unit 15, a controller 17, an input unit 19, and a display 21. Note that the medical image observation apparatus of this embodiment can operate even without the memory unit 15. At this time, medical images received from the medical image generation apparatus 1 and the database server 3 are displayed on the display screen of the display 21 under the control of the controller 17 to be described below.

The data receiver 11 receives, via the LAN, a plurality of medical image data stored in the database server 3 or medical image data generated by the medical image generation apparatus 1. The data receiver 11 transmits a medical image added with an annotation and input via the input unit 19 to the database server 3 via the LAN.

The memory unit 15 includes a RAM (Random Access Memory) formed from a semiconductor integrated circuit, a semiconductor memory device such as a Flash SSD (Solid State Disk) that is a semiconductor memory element, or an HDD. The memory unit 15 temporarily stores a plurality of medical image data received by the data receiver 11 and data associated with the medical image data based on an operator instruction input via the input unit 19.

The controller 17 comprises a central processing unit (to be referred to as a CPU hereinafter) (not shown) and a storage circuit. The controller 17 stores, in the storage circuit, a rule (to be referred to as a layout rule hereinafter) to be used to lay out a plurality of medical images stored in the memory unit 15 on the display screen of the display 21 based on an operator instruction input via the input unit 19. The layout rule will be described later in detail. The controller 17 stores, in the storage circuit, a rule (to be referred to as a scroll rule hereinafter) to be used to scroll the medical images arrayed on the display screen of the display 21 based on an operator instruction input via the input unit 19. The scroll rule will be described later in detail.

The controller 17 reads out a plurality of medical image data selected based on an operator instruction input via the input unit 19 from the database server 3 and writes them in the memory unit 15. The controller 17 reads out some of the plurality of medical image data written in the memory unit 15 in accordance with the layout rule read out from the storage circuit based on the display scanning method of the display 21. Note that the controller 17 may control at least one of data write and data read to lay out the plurality of medical images selectively read out from the database server 3 on the display screen in accordance with at least one of the scroll rule and the layout rule set by the operator. The controller 17 may also control at least one of data write and data read to remove a medical image laid out on the display screen in accordance with at least one of the scroll rule and the layout rule set by the operator. The controller 17 may also control at least one of data write and data read to remove a medical image laid out on the display screen and almost simultaneously lay out a medical image on the display screen in accordance with at least one of the scroll rule and the layout rule set by the operator. The controller 17 may also control at least one of data write and data read to replace a medical image laid out on the display screen with a medical image selected by the operator (for example, a medical image stored in the database server 3).

When setting the layout rule and the scroll rule, the controller 17 divides the display screen of the display 21 into a region (to be referred to as a display region hereinafter) where a medical image is displayed at a certain moment of interpretation and a region (to be referred to as a non-display region hereinafter) where no medical image is displayed at a certain moment of interpretation. Note that the display screen division can be set based on an operator instruction input via the input unit 19. The controller 17 can also set a plurality of blocks for setting the display order of a plurality of medical images in, for example, the memory unit 15 and set a specific block out of the plurality of blocks as a display block. Note that the entire display block corresponds to the display region, and the blocks out of the plurality of blocks except the display block correspond to the non-display region.

The layout rule will be described below. The layout rule is a rule to control data read from the memory unit 15 to lay out a plurality of medical images stored in the memory unit 15 on the display screen of the display 21. More specifically, the display screen of the display 21 is divided into a plurality of n×m display frames (n and m are integers of 1 or more) under the layout rule. The size of each display frame corresponds to the size of the medical image to be displayed. Note that the size of the display frame can be set to a display frame size desired by the operator. The plurality of medical images selected by the operator via the input unit 19 are classified into a plurality of groups in accordance with at least one of, for example, the type of the medical image generation apparatus 1, the image generation method, the imaging condition, the imaging position, the operator instruction, the operator setting, and the imaging date/time. The plurality of classified medical images are arrayed on the display screen of the display 21 for each group. The operator setting means causing the operator to set in advance information to be classified into groups using the information of the tag of additional information of the medical images in, for example, the DICOM standard. A plurality of medical images having the set information are handled as one group.

The display screen (to be referred to as a setting screen hereinafter) when setting the layout rule and the scroll rule is divided into a display region and a non-display region. The size of each of the plurality of frames in the display region of the setting screen is smaller than the size of each of the plurality of display frames at the time of interpretation. The non-display region is set by extending the plurality of (n rows×m columns) frames belonging to the display region to the periphery. A plurality of medical images are arrayed for each group in the plurality of frames of the display region of the setting screen and the plurality of frames of the non-display region based on an operator instruction input via the input unit 19. The medical images arrayed in the plurality of frames of the display region can be replaced or exchanged with the medical images arrayed in the plurality of frames of the non-display region based on an operator operation input via the input unit 19. In addition, the medical images arrayed in the plurality of frames of the display region can also be replaced with the medical images stored in the database server 3 based on an operator operation input via the input unit 19. Note that the size of each of the plurality of frames in the display region does not change during scroll of the medical images. That is, in medical image scroll to be described below, removing a medical image from the display screen and laying out, on the display screen, a medical image that is not arrayed on the display screen are almost simultaneously controlled by the controller 17.

The detailed medical image array direction based on the layout rule will be described in detail concerning the following operation. Note that the operator can arbitrarily change the layout rule. More specifically, the operator can set, via the input unit 19, the direction and order of arraying the plurality of classified medical images on the display screen for each group. Note that the plurality of medical images belonging to the plurality of groups may be sequenced via the input unit 19. Each of the plurality of groups to classify the plurality of medical images may be a series complying with the DICOM standard.

The scroll rule will be described below. The scroll rule is a rule to control data read from the memory unit 15 to scroll a plurality of medical images arrayed on the display screen or a plurality of undisplayed medical images on the group basis. The medical images are scrolled under the scroll rule in the direction in which the medical images are arrayed based on the layout rule. Note that the scroll direction may be reverse to the array direction. The medical images arrayed in the non-display region are thus displayed on the display screen. Note that the group to which the medical images to be scrolled may be selected based on an operator instruction input via the input unit 19. In addition, the direction in which the medical images are scrolled may be set based on an operator instruction input via the input unit 19. The detailed scroll direction based on the scroll rule will be described in detail concerning the following operation. Note that when each of the plurality of groups is a series complying with the DICOM standard, the scroll rule is set to scroll the medical images for each series. The controller 17 scrolls the plurality of medical images displayed on the display 21 for each group in accordance with the scroll rule read out from the storage circuit based on a scroll instruction input by the operator.

Note that the controller 17 can also set the display order of the plurality of medical images corresponding to the scroll rule for the plurality of blocks and arrange the plurality of medical images in the plurality of blocks in accordance with the set display order. At this time, the controller 17 controls the display 21 to arrange display target medical images out of the plurality of medical images in the display blocks based on the display order in accordance with a scroll instruction input by the operator via the input unit 19.

The controller 17 controls the data read from the memory unit 15 to replace displayed medical images between a plurality of display screens of the display 21. More specifically, the operator selects, via the input unit 19, a first medical image and a second medical image to be replaced between different display screens. In the first group to which the first medical image belongs and the second group to which the second medical image belongs, the medical images are replaced such that the first medical image belongs to the second group, and the second medical image belongs to the first group. Changing the groups to which the images belong corresponds to changing the layout rule. The controller 17 controls the data read from the memory unit 15 in accordance with the changed layout rule. Note that the number of medical images to be replaced is not limited to two.

Note that the read control of the controller 17 may be write control in the frame memory (not shown) of the display 21. At this time, the display region and the non-display region are provided on the frame memory.

The input unit 19 inputs various kinds of instructions, commands, information, selections, and settings from the operator to the controller 17. The input unit 19 includes an input device formed from a trackball, switch buttons, a mouse, and a keyboard to set the layout rule and the scroll rule, select a plurality of medical image data, instruct scroll, select medical images to be replaced, and divide the setting screen. Note that the input device may be a touch panel provided to cover the display screen.

More specifically, the input unit 19 inputs, for example, a selection instruction to select a plurality of medical image data stored in the database server 3, a condition to classify a plurality of medical images into a plurality of groups in the layout rule, a direction in which the plurality of medical images are arrayed on the display screen, a direction in which the medical images are scrolled on the group basis, and the display order to the controller 17 in accordance with the operation of the input device by the operator.

The display 21 displays, on the display screen, data read out from the memory unit 15. Note that the display 21 may have a plurality of display screens. The display 21 displays a setting screen to assign a plurality of medical images to the display region and the non-display region and lay out them for each group.

(Operation)

Figure 3:
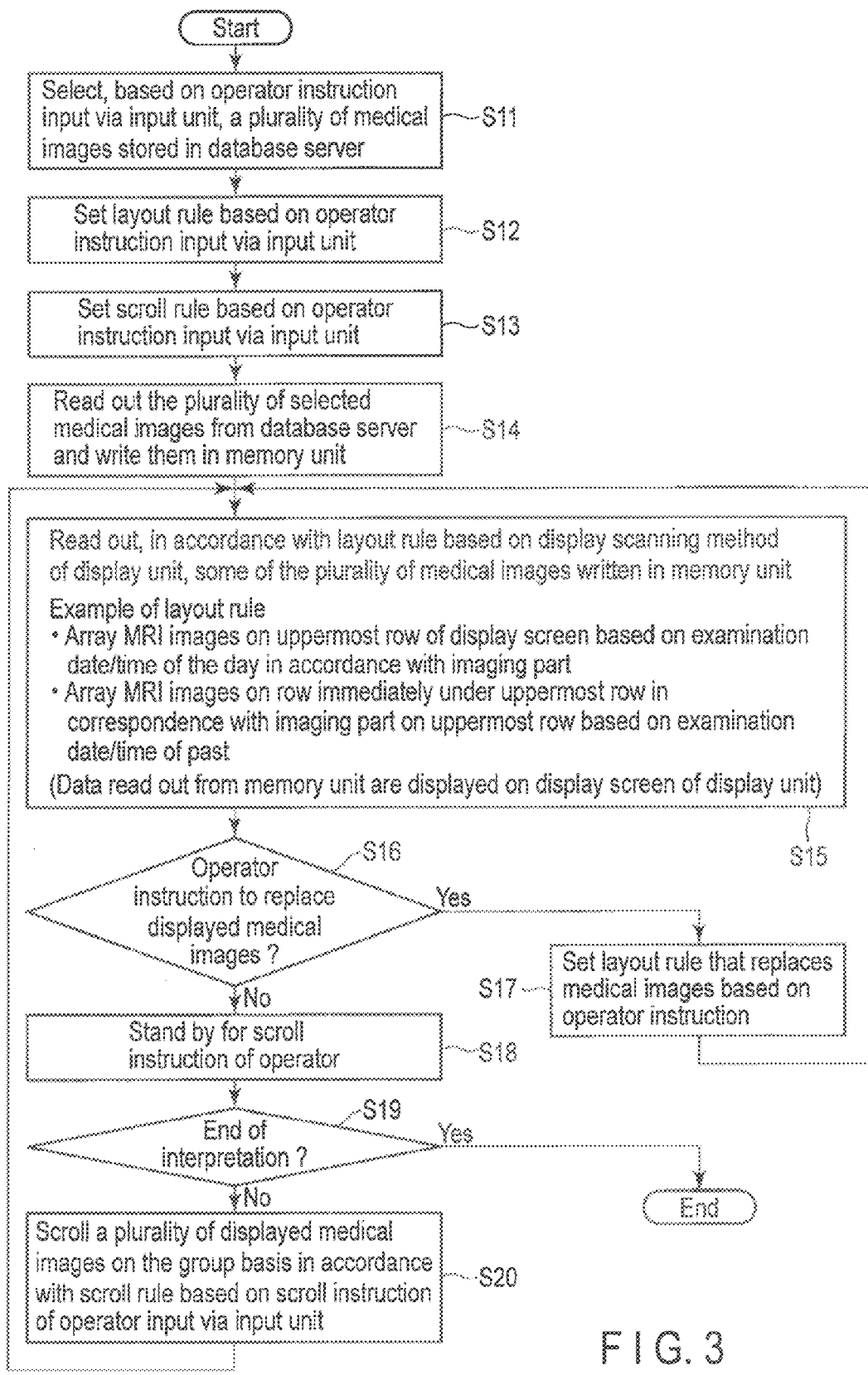
FIG. 3 is a flowchart illustrating a procedure of causing the medical image observation apparatus to display a medical image needed by an interpretation doctor according to the embodiment.

An operation of displaying, on the display screen of the display 21, some of a plurality of medical image data selectively read out based on an operator instruction and an operation of scrolling a plurality of displayed medical images to display medical images arrayed in the non-display region on the display screen of the display 21 in the medical image observation apparatus 7 will be described next with reference to the flowchart shown in FIG. 3.

Data of a plurality of medical images or the like stored in the database server 3 are selected based on an operator instruction input via the input unit 19 (step S11). The controller 17 reads out the layout rule from the storage circuit under a setting based on an operator instruction input via the input unit 19 (step S12). The controller 17 reads out the scroll rule from the storage circuit under a setting based on an operator instruction input via the input unit 19 (step S13). Note that steps S11 to S13 may be executed not in particular order. The layout rule and the scroll rule may be set, based on an operator instruction input via the input unit 19, for the setting screen or a plurality of display blocks displayed on the display 21.

Figure 4:
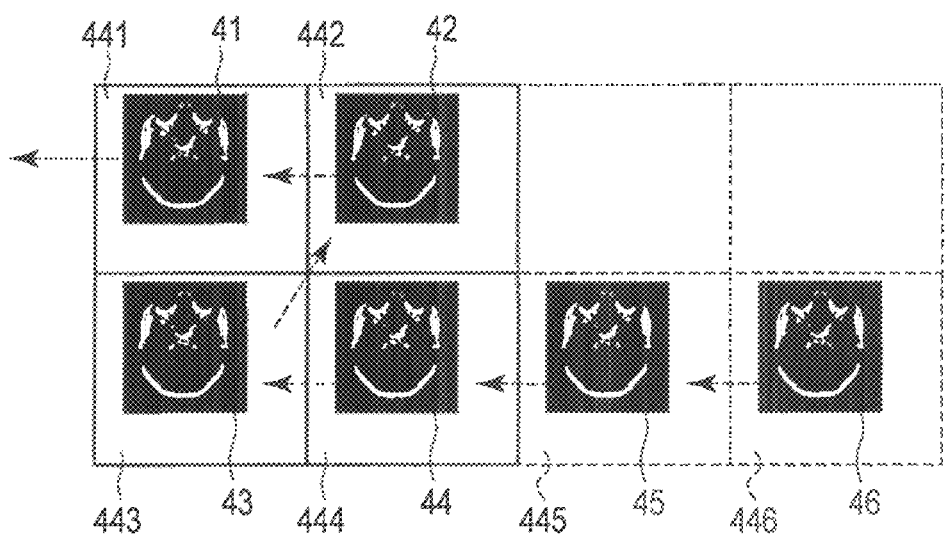
FIG. 4 is a view showing an example of a plurality of medical images arrayed for each group and a display screen for setting a scroll direction according to the embodiment.

FIG. 4 shows an example of a setting screen that displays a set scroll direction and a plurality of medical images arrayed for each group based on a preset layout rule. Medical images 41 to 46 shown in FIG. 4 belong to groups 1 to 6, respectively. Frames 441 to 444 surrounded by solid lines represent a display region displayed on the display screen of the display 21 at the time of interpretation. Frames 445 and 446 surrounded by dotted lines represent a non-display region that is not displayed on the display screen of the display 21 at the time of interpretation. Scroll target medical images are arranged in the frames of the display region and the non-display region. The arrows indicate the scroll direction of the medical images 41 to 46. At the time of interpretation, the medical images 41 to 44 shown in FIG. 4 are first displayed on the display screen of the display 21.

When the operator inputs a scroll instruction via the input unit 19, the medical images are scrolled for each group along the direction of arrows. At this time, the medical image 42 is arranged in the frame 441, the medical image 43 is arranged in the frame 442, the medical image 44 is arranged in the frame 443, and the medical image 45 is arranged in the frame 444 and displayed on the display screen of the display 21. In addition, the medical image 46 is arranged in the frame 445. At almost the same time as the medical image arrangement in this scroll, the medical image 41 is removed from the display screen. More specifically, the medical images 42 to 45 stored in the memory unit 15 are arrayed in the frames 441 to 444 and displayed on the display screen of the display 21 under the read control of the controller 17 in accordance with the layout rule and the scroll rule.

When the operator further inputs a scroll instruction via the input unit 19, the medical images are scrolled for each group along the direction of arrows. At this time, the medical image 43 is arranged in the frame 441, the medical image 44 is arranged in the frame 442, the medical image 45 is arranged in the frame 443, and the medical image 46 is arranged in the frame 444 and displayed on the display screen. At almost the same time as the medical image arrangement in this scroll, the medical image 42 is removed from the display screen. More specifically, the medical images 43 to 46 stored in the memory unit 15 are arrayed in the frames 441 to 444 and displayed on the display screen of the display 21 under the read control of the controller 17 in accordance with the layout rule and the scroll rule.

Figure 5:
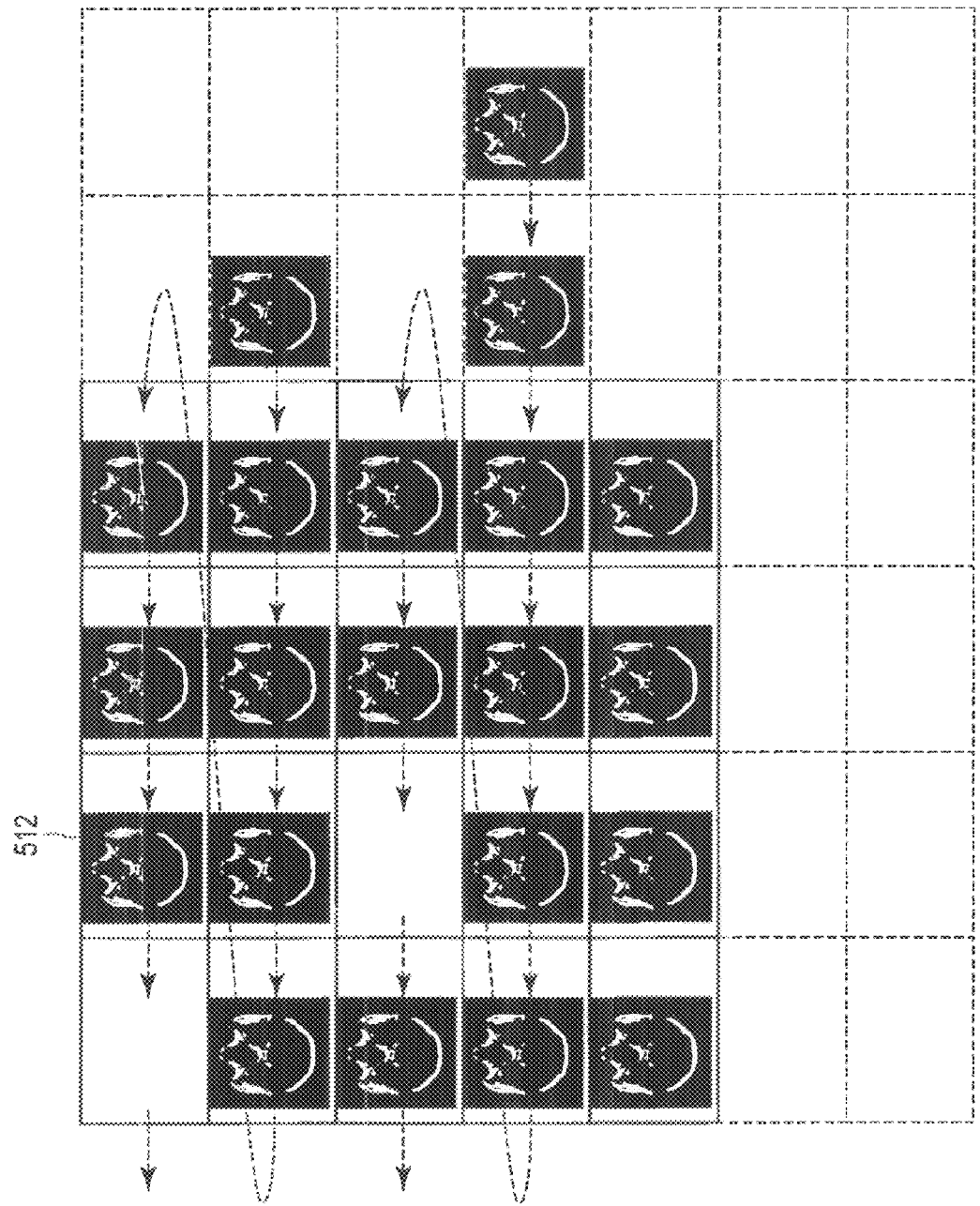
FIG. 5 is a view showing an example of a plurality of medical images arrayed for each group based on a preset layout rule and a display screen for setting a plurality of scroll directions according to the embodiment.

FIG. 5 shows an example of a setting screen that displays a plurality of scroll directions and a plurality of medical images arrayed for each group based on a preset layout rule. A plurality of frames surrounded by solid lines represent a display region displayed on the display screen of the display 21 at the time of interpretation. Frames surrounded by dotted lines represent a non-display region where no medical images are arrayed on the display screen of the display 21 at the time of interpretation. Arrows indicate the scroll direction of the first and second rows and that of the third and fourth rows. Note that the scroll rule may be set not to scroll the images as in the fifth row in FIG. 5.

FIG. 6 is a view showing an example of additional information of a plurality of medical images that are arrayed, using the additional information of the medical images, on the display screen divided into a display region and a non-display region. A plurality of frames surrounded by solid lines in FIG. 6 represent a display region where the medical images are displayed on the display screen. A plurality of frames surrounded by dotted lines in FIG. 6 represent a non-display region where no medical images are arrayed on the display screen. The size and the total number of frames of each of the display region and the non-display region can arbitrarily be set based on an operator instruction input via the input unit 19. The plurality of medical images can also be arranged for each group in each of the display region and the non-display region based on an operator instruction input via the input unit 19. Note that in the setting screen, the medical images to be scrolled may be associated by, for example, numbers. FIG. 6 also illustrates an example of setting display for setting the same layout as in FIG. 5 based on the additional information of each of the plurality of medical images arrayed for each group. For example, the additional information of a medical image 512 on the first row and second column represents that the examination is CT of the day, the group to which the medical image belongs is group 1, and the medical image is the first image of group 1. The first image of group 1 is based on sequencing of the plurality of medical images belonging to group 1. Note that if the plurality of medical images belonging to a group are not sequenced, each medical image may be specified based on additional information by the DICOM standard or the like. The layout may be done not to arrange any medical image in the display frames on the first row and first column and the third row and second column, as in FIGS. 5 and 6.

After step S13, the controller 17 reads out the plurality of selected medical images from the database server 3 via the data receiver 11 and writes them in the memory unit 15 (step S14). Subsequently, the controller 17 reads out some of the plurality of medical image data written in the memory unit 15 in accordance with the set layout rule based on the display scanning method of the display 21 (step S15). Some medical images are medical images out of the plurality of selected medical images in a number (n×m) corresponding to the plurality of display frames or display blocks. As the layout rule, for example, MR images are arrayed on the uppermost row of the display screen based on the examination date/time of the day in accordance with the imaging part. Other MR images are arrayed on the row immediately under the uppermost row of the display screen in correspondence with the imaging part on the uppermost row based on the examination date/Lime of the past. Under this layout rule, the operator can comparatively interpret the MRI images arrayed on the uppermost row of the display screen and the row immediately under it for each imaging part.

When the operator inputs, via the input unit 19, an instruction to replace the medical images displayed on different display screens (step S16), a layout rule that replaces the medical images is set based on an operator instruction (step S17). FIG. 7 is a view showing an example in which a medical image on display screen 1 and a medical image on display screen 2 are replaced with each other. When the operator selects, via the input unit 19, medical images displayed on different display screens, a layout rule that replaces the selected medical images is set.

If the operator inputs, via the input unit 19, no instruction to replace the medical images displayed on the plurality of display screens (step S16), the controller 17 stands by for a scroll instruction of the operator (step S18). During the standby, the display screen stands still. If the operator inputs not an interpretation end instruction (step S19) but a scroll instruction via the input unit 19, the controller 17 scrolls the plurality of displayed medical images on the group basis in accordance with the set scroll rule (step S20). The operation from the processing of reading out some of the plurality of medical images written in the memory unit 15 in accordance with the set layout rule based on the display scanning method of the display 21 (step S15) to the processing of scrolling the plurality of displayed medical images on the group basis (step S20) is repeated until the end of interpretation is selected (step S19). Drawings that illustrate examples of the layout rule and the scroll rule will be explained below.

Figure 8:
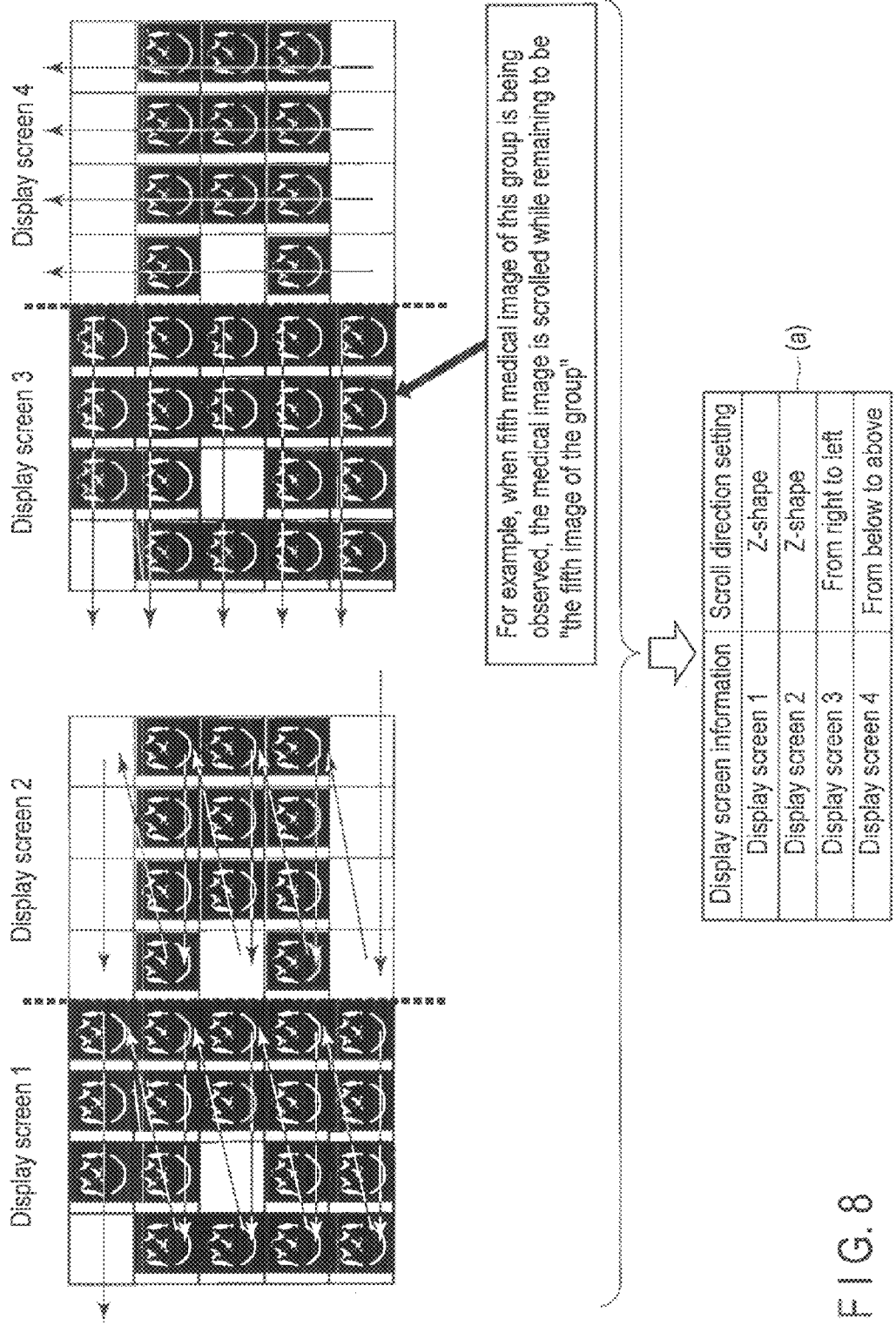
FIG. 8 is a view showing an example in which all medical images arrayed for each group on a plurality of display screens are scrolled on the display screens on the group basis in accordance with a scroll instruction of an operator for each display screen according to the embodiment.

FIG. 8 is a view showing an example in which all medical images arrayed for each group on a plurality of display screens are scrolled on the display screens on the group basis in accordance with a scroll instruction of the operator for each display screen. On display screens 1 and 2 shown in FIG. 8, the plurality of medical images are arrayed in the direction from the display frame on the fifth row and fourth column to that on the fifth row and first column, from the display frame on the fifth row and first column to that on the fourth row and fourth column, from the display frame on the fourth row and fourth column to that on the fourth row and first column, from the display frame on the fourth row and first column to that on the third row and fourth column, from the display frame on the third row and fourth column to that on the third row and first column, from the display frame on the third row and first column to that on the second row and fourth column, from the display frame on the second row and fourth column to that on the second row and first column, from the display frame on the second row and first column to that on the first row and fourth column, and from the display frame on the first row and fourth column to that on the first row and first column. The array direction of this type will be referred to as a Z type.

The plurality of medical images on display screens 1 and 2 in FIG. 8 are scrolled for each group in the Z shape. No medical images are arrayed in the empty display frames of display screens 1 to 4. The plurality of medical images displayed on display screen 3 in FIG. 8 are arrayed on each row in the direction from the right end of display screen 3 to the left end of display screen 3 and scrolled. On display screen 3 shown in FIG. 8, if the medical image displayed in the display frame on the fifth row and third column is the fifth image of the group to which the medical image belongs, the medical image displayed in the display frame on the fifth row and third column is scrolled while remaining to be the fifth image of the group. The plurality of medical images displayed on display screen 4 in FIG. 8 are scrolled on each row in the direction from the lower end of display screen 4 to the upper end of display screen 4. FIG. 8(*a*) is a list of the plurality of display screens and the scroll directions of the medical images.

FIG. 9 is a view showing an example in which some of the medical images arrayed on a plurality of display screens are scrolled on the display screens on the group basis in accordance with a scroll instruction of the operator for each display screen. Display screens 1 and 3 in FIG. 9 show the first to third rows on which the plurality of medical images are scrolled in different directions, and the fourth and fifth rows on which the medical images arc not scrolled. On display screen 1 in FIG. 9, the plurality of medical images on the first row are arrayed from the right end of display screen 1 to the left end of display screen 1 and scrolled for each group. The plurality of medical images on the second row are arrayed from the left end of display screen 1 to the right end of display screen 1 and scrolled for each group. The plurality of medical images on the third row are arrayed from the right end of display screen 1 to the left end of display screen 1 and scrolled for each group. The plurality of medical images on display screen 2 shown in FIG. 9 are arrayed in the Z shape and scrolled for each group. On display screen 3 in FIG. 9, the plurality of medical images on the first and second rows are arrayed from the right end of display screen 3 to the left end of display screen 3 and scrolled for each group. The plurality of medical images on the third row are arrayed from the left end of display screen 3 to the right end of display screen 3 and scrolled for each group. The medical images on display screen 4 shown in FIG. 9 are arrayed in a direction parallel to the direction (to be referred to as a diagonal direction hereinafter) from the lower right corner of display screen 4 to the upper left corner of display screen 4 and scrolled.

FIG. 9(*a*) is a list of the plurality of display screens, row/column information representing rows/columns on which the medical images are scrolled for each group, and the directions in which the medical images are scrolled for each group. As compared to FIG. 8(*a*), the scroll row/column information is added in FIG. 9(*a*). The scroll row/column information is the information of scroll rows/columns set by the operator via the input unit 19. The scroll row/column information enables to set scroll for each row of the plurality of display frames divided into n rows and m columns.

Note that when there exist two display screens, as shown in FIG. 7, one medical image may be displayed on one display screen (for example, display screen 2), and a plurality of medical images may be displayed on the other display screen (for example, display screen 1).

(First Modification)

The first modification is different from the embodiment in that removing a group in which the number of medical images is smaller than a predetermined number from the display target is added to the layout rule of the embodiment.

The input unit 19 inputs a condition to remove a medical image from the display target to the controller 17.

The controller 17 removes each group in which the number of medical images is smaller than a predetermined number from the display target. More specifically, the controller 17 stores, in the storage circuit, a predetermined number set by the operator via the input unit 19. The controller 17 counts the number of medical images belonging to each of the plurality of groups to which the medical images are classified under the layout rule. The controller 17 does not read out, from the memory unit 15, medical images belonging to a group in which the counted number of medical images is smaller than the predetermined number. Note that the controller 17 may set in advance a plurality of display frames in which no medical images can be arrayed and a plurality of frames not to be displayed based on an operator instruction input via the input unit 19 in accordance with the storage capacity of the memory unit 15.

Figure 10:
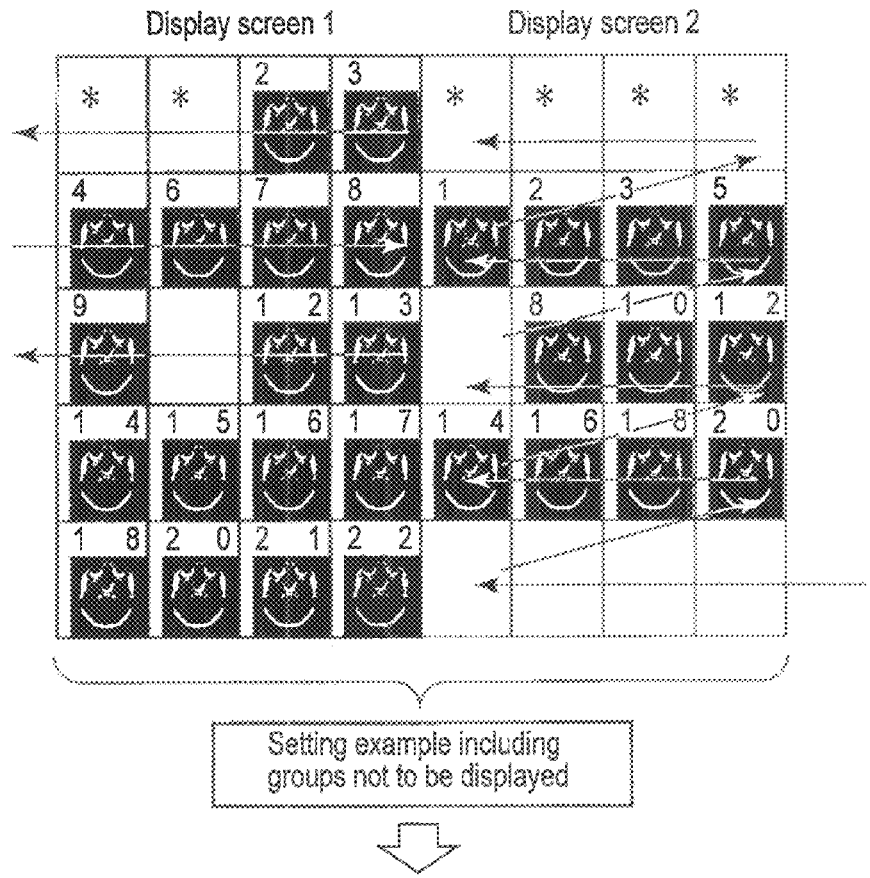
FIG. 10 is a view showing an example in which a group in which the number of medical images is smaller than a predetermined number is removed from the display target according to the embodiment.

FIG. 10 is a view showing an example in which a group in which the number of medical images is smaller than a predetermined number is removed from the display target, and the medical images are arrayed for each group. An asterisk in FIG. 10 indicates a display frame preset in accordance with the storage capacity of the memory unit 15 in which no medical image can be arrayed. FIG. 10(a) is a list of the plurality of display screens, row/column information representing rows/columns on which the medical images are scrolled, the directions in which the medical images are scrolled, and group display information. As compared to FIG. 9(a), the group display information is added in FIG. 10(a). The group display information is a predetermined condition set by the operator via the input unit 19. A group that does not satisfy the predetermined condition is removed from the display target. For example, group display information "two or more" means that when the number of medical images belonging to a group is two or more, the medical images of this group are displayed on the display screen. Group display information "two or less" means that when the number of medical images belonging to a group is two or less, the medical images of this group are displayed on the display screen. Group display information "except annotation images" means that out of medical images belonging to a group, only medical images without an annotation are displayed on the display screen.

(Second Modification)

The second modification is different from the embodiment in that when scrolling medical images having annotations on the group basis, the annotations are displayed in synchronism with the elapse of a predetermined time from the stop of medical image scroll.

The input unit 19 inputs setting of a predetermined time from the operator to the controller 17.

When scrolling medical images having annotations, the controller 17 controls data read from the memory unit 15 so as to display the annotations on the medical images in synchronism with the elapse of the predetermined time from the stop of medical image scroll. More specifically, the controller 17 stores, in the storage circuit, a predetermined time set by the operator via the input unit 19. Using the stop of medical image scroll as a trigger, the controller 17 reads out the annotations added to the medical images from the memory unit 15 in synchronism with the elapse of the predetermined time. The readout annotations are superimposed on the scrolled medical images. The predetermined time will be described below.

Figure 11:
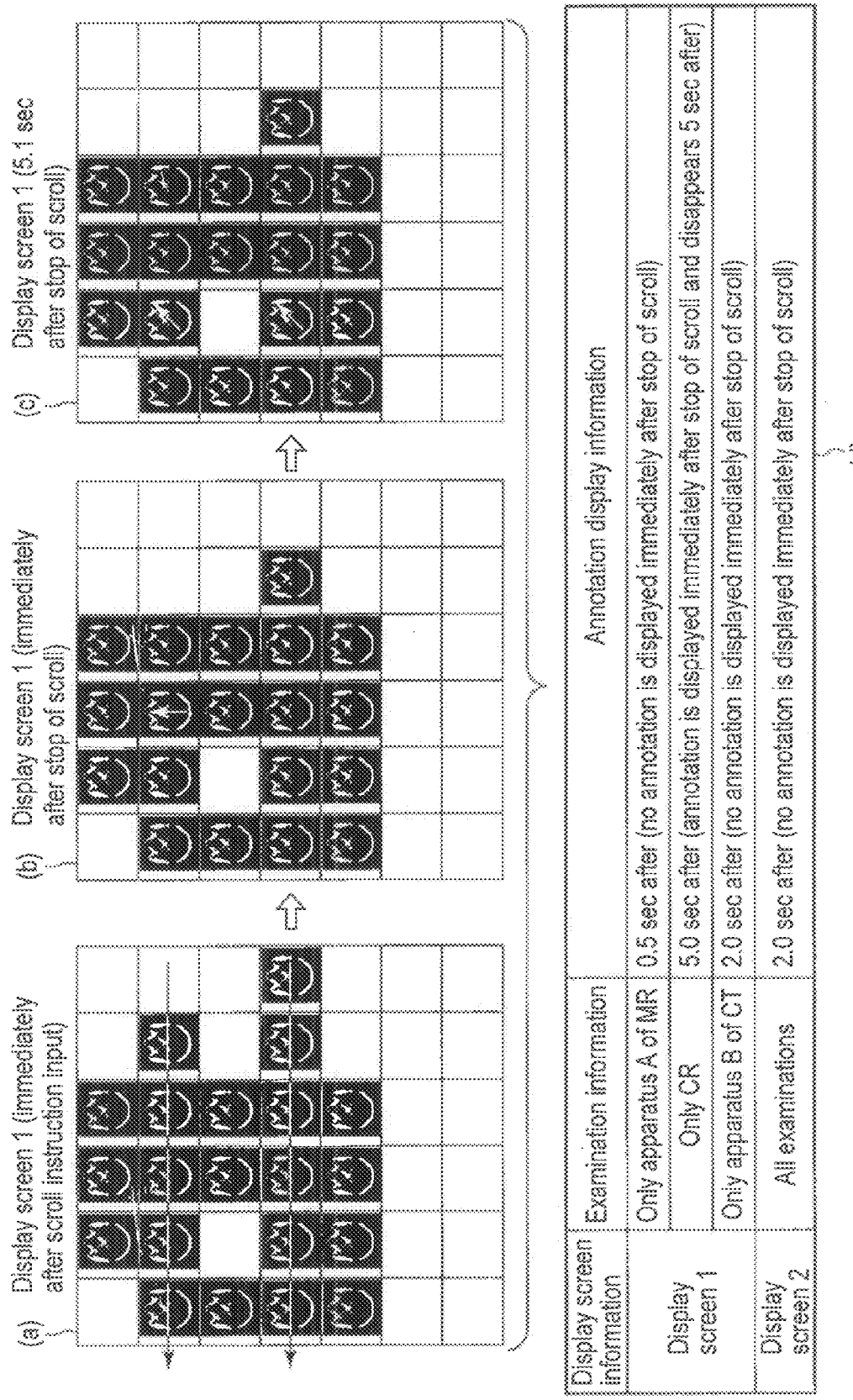
FIG. 11 is a view showing an example in which when medical images with annotations are scrolled on the group basis, the annotations are displayed in synchronism with the elapse of a predetermined time according to the embodiment.
Figure 13:
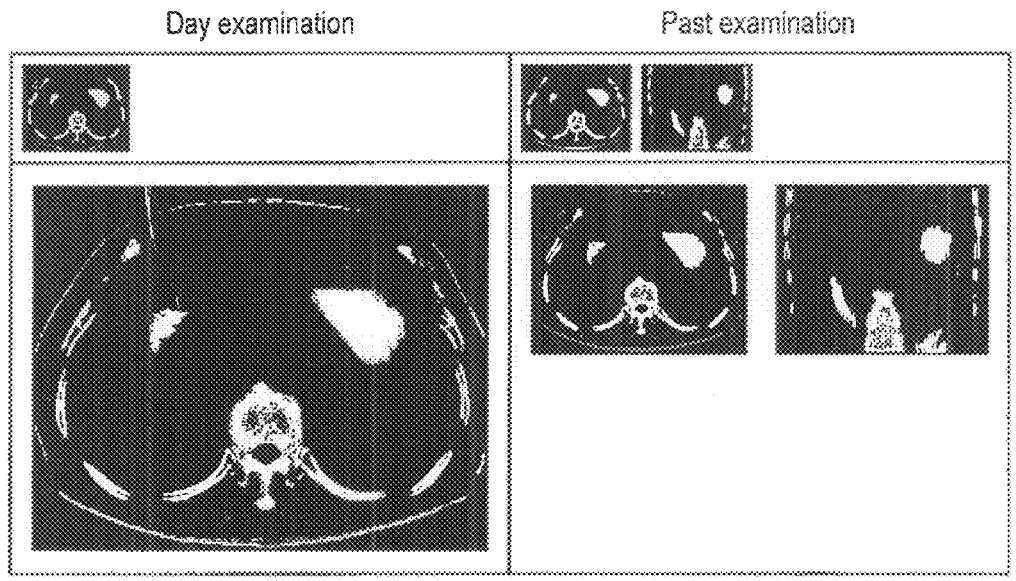
FIG. 13 is a view showing an example of a display screen on which a plurality of medical images are displayed in a conventional image observation apparatus.
Figure 14:
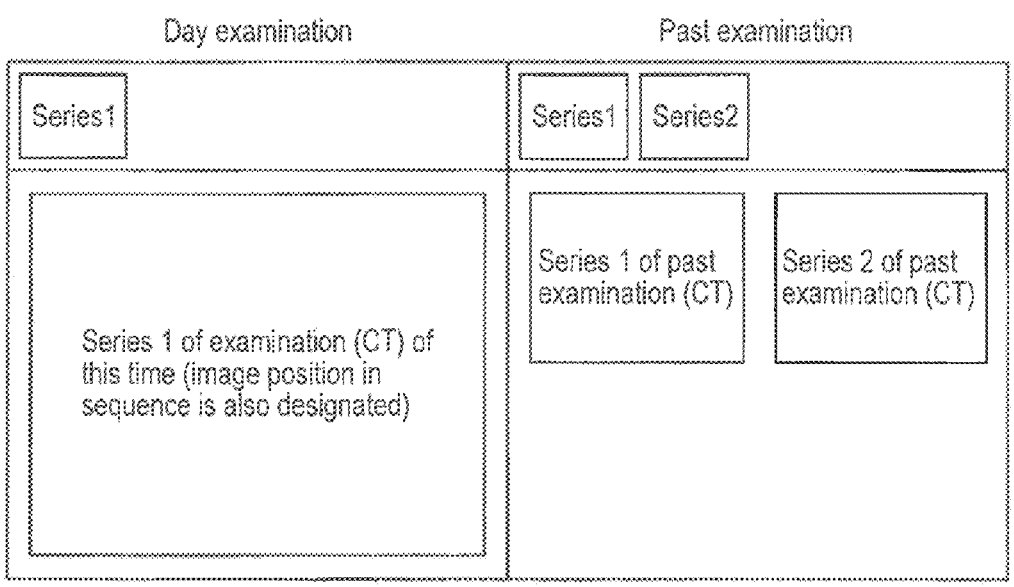
FIG. 14 is a view showing the additional information of the medical images shown in FIG. 13 in the conventional image observation apparatus.

FIG. 11 is a view showing an example of a time series on display screen 1 when medical images having annotations are scrolled on the group basis, and the annotations are displayed in synchronism with the elapse of a predetermined time. FIG. 11(a) shows display screen 1 immediately after the operator has input a scroll instruction via the input unit 19. At this time, the annotations added to the medical images are not displayed. Each arrow on display screen 1 in FIG. 11(a) indicates the medical image scroll direction. FIG. 11(b) shows display screen 1 immediately after the stop of medical image scroll.

The hollow arrow on display screen 1 in FIG. 11(b) indicates the annotation displayed immediately after the stop of medical image scroll. FIG. 11(c) shows display screen 1 when 5.1 sec has elapsed from the stop of medical image scroll. The hollow arrows on display screen 1 in FIG. 11(c) indicate the annotations displayed 0.5 sec and 2.0 sec after the stop of medical image scroll, respectively.

FIG. 11(d) is a list of display screen information, examination information, and annotation display information. The annotation display information represents the time from the stop of medical image scroll to the display of annotations or the time during which the annotations are displayed since immediately after the stop of medical image scroll. The time from the stop of medical image scroll to the display of annotations or the time during which the annotations are displayed since immediately after the stop of medical image scroll corresponds to the predetermined time. For example, when the examination information is "only apparatus A of MR", the annotation display information represents that the annotation is displayed 0.5 sec after the stop of scroll. When the examination information is "only apparatus B of CT", the annotation display information represents that the annotation is displayed 2.0 sec after the stop of scroll. When the examination information is "only computed radiography (to be referred to as CR hereinafter)", the annotation display information represents that the annotation is displayed only for 5.0 sec since immediately after the stop of scroll. The annotation displayed for 5.0 sec since immediately after the stop of scroll disappears 5.0 sec after the stop of scroll.

Note that as shown in FIG. 11(d), annotation display information concerning display screen 2 (not shown in FIG. 11) may be set independently of display screen 1.

(Third Modification)

The third modification is different from the embodiment in that when a pointer is located within a predetermined range of the display screen of the display 21, medical image scroll is started or ended based on an operator instruction, and medical images that are not arrayed on the display screen are laid out on the display screen of the display 21 based on an operator instruction input via the input unit 19.

The input unit 19 inputs the setting of a predetermined range from the operator to the controller 17.

When a pointer is located within the predetermined range of the display screen of the display 21, the controller 17 starts or ends medical image scroll based on an operator instruction. At this time, the controller 11 controls data read from the memory unit 15 so as to lay out medical images that are not arrayed on the display screen on the display screen of the display 21 based on an operator instruction input via the input unit 19. The predetermined range indicates, for example, a plurality of regions obtained by virtually dividing the display screen or a plurality of display frames, a region where one of a plurality of displayed medical images is displayed, or a region set by the operator where a plurality of medical images are displayed. The following explanation will be done assuming that the predetermined range is obtained by virtually dividing the display screen into two regions. Note that the predetermined range may indicate each of a plurality of medical images displayed on the display screen or a region obtained by dividing each of a plurality of medical images displayed on the display screen.

The display screen of the display 21 is virtually divided into two regions based on an operator instruction input via the input unit 19. Note that the number of divided regions is not limited to two. When the pointer is located in one of the two divided regions, the controller 17 starts or ends medical image scroll based on an operator instruction. Note that the region where the scroll is started or ended based on an operator instruction can be set based on an operator instruction input via the input unit 19. Based on the operator instruction input via the input unit 19, the controller 17 controls data read from the memory unit 15 so as to lay out, on the display screen, medical images that are not displayed but included in the group to which the medical images displayed on the display screen belong (to be referred to as image flick hereinafter).

FIG. 12 is a view showing an example of the boundary between a region where the image flick of medical images is executed and a region where the medical images are scrolled based on the position of the pointer on the display screen divided into two areas. The double line that connects the lower right corner of the display screen and the upper left corner of the display screen in FIG. 12 represents the boundary. The arrow on each row of the display screen shown in FIG. 12 indicates the direction in which the medical images are scrolled. Each arrow larger than the arrow indicating the scroll direction in FIG. 12 indicates the pointer. If the pointer is located on the upper right side of the double line on the display screen shown in FIG. 12, the plurality of medical images displayed on the display screen are scrolled along the scroll direction shown in FIG. 12 based on an operator instruction input via the input unit 19. If the pointer is located on the lower left side of the double line on the display screen shown in FIG. 12, medical image scroll is started or ended based on an operator instruction. Medical images that are not displayed on the display screen but included in the group to which the plurality of medical images displayed on the display screen belong are displayed on the display screen based on an operator instruction input via the input unit 19. Note that the medical image group in the explanation of FIG. 12 indicates a group.

Note that the cancel state of scroll of a group of a plurality of medical images (to be referred to as a scroll cancel state hereinafter) can be set based on an operator instruction input via the input unit 19. The scroll cancel state is set when, for example, the operator is not pressing the shift key of the keyboard, a medical image is selected and set in the active state by the operator, or the pointer is located on a displayed medical image. At this time, the controller 17 executes image flick based on an operator instruction input via the input unit 19. The operator instruction means, for example, operating the wheel without pressing the shift key. A scroll execution state is set when, for example, the operator is pressing the shift key, no medical image is active, or the pointer is not located on a displayed medical image. At this time, the controller 17 executes scroll based on an operator instruction input via the input unit 19. The operator instruction means, for example, operating the wheel while pressing the shift key.

The effects of the embodiment and the first to third modifications will be summarized below.

According to the medical image observation apparatus 7, the display frame set to the size desired by the operator is extended to set a plurality of frames where no medical images are arrayed on the display screen. The medical image observation apparatus 7 classifies a plurality of medical images selected by the operator via the input unit 19 into a plurality of groups in accordance with at least one of, for example, the type of the medical image generation apparatus 1, the image generation method, the imaging condition, the imaging position, the operator instruction (for example, private tag information of DICOM), and the imaging date/Lime. The classified medical images are arrayed on in the plurality of display frames or the plurality of frames on the display screen of the display 21 for each group. The medical image observation apparatus 7 scrolls the plurality of medical images arrayed on the display screen or a plurality of medical images that are not arrayed on the display screen on the group basis in the scroll direction set by the operator via the input unit 19. Medical images that are located in the frames where no medical images are arrayed on the display screen are thus displayed on the display screen. With the above-described arrangement, the medical image observation apparatus can display a medical image, which could not be displayed on the display screen, in the size desired by the operator.

In addition, the operator can set the layout rule and the scroll rule. It is therefore possible to improve the operability of the medical image observation apparatus 7 and reduce the operation load on an interpretation doctor or the like. Furthermore, when observing a medical image with an annotation, the annotation is not displayed during scroll of the medical image. This allows to reduce flicker on the display screen during scroll and thus reduce the load on the interpretation doctor or the like.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image observation apparatus, comprising:
a data receiver configured to receive a plurality of medical images, each of the plurality of medical images including additional information comprising examination information, identifier information of an imaged patient including an examination identifier and series identifier, and an image identifier unique to each medical image of said plurality; and
a controller configured to execute a display control process for selecting at least one medical image to be interpreted from the plurality of medical images,
wherein the controller, as part of the display control process, is further configured to execute control to:
classify the plurality of medical images into medical image groups in accordance with a predetermined condition that includes classification information from each of the plurality of medical images, said classification information comprising a type of image generator, image generation method, imaging condition, imaging position, external input, and said identifier information, display images, each of which is selected from each of the classified medical image groups, on a display screen, replace a combination of the selected images displayed on the display screen with another combination of selected images by an input scroll operation, wherein annotations comprising at least one of the additional information and the classification information are displayed with said another combination of selected images in synchronism with an elapse of a predetermined time from a stop of the input scroll operation, and replace only one of the selected images displayed on the display screen with another selected but previously undisplayed one image belonging to a same medical image group by a different input flick operation, on an image-by-image basis within the selected images of the displayed classified medical image groups, wherein on the display screen divided into a plurality of n row x m column display frames, n and m being integers of 1 or more, the medical images are arrayed in a direction obtained by repeating, from a display frame on an nth row and mth column to a display frame on a first row and first column, a procedure of arraying the medical images from the display frame on the nth row and mth column at a corner of the display screen to a display frame on an nth row and first column and subsequently arraying the medical images from a display frame on an (n−1)th row and mth column to a display frame on an (n−1)th row and first column, and the arrayed medical images are scrolled in the array direction or in a direction reverse to the array direction.

2. The medical image observation apparatus according to claim 1, wherein the controller is further configured to execute control to:

lay out other medical images, which are not arrayed on the display screen, on the display screen in accordance with a preset scroll direction;

remove, from the display screen, the other medical images laid out on the display screen; or remove, from the display screen, the other medical images laid out on the display screen, and lay out the other medical images, which are not arrayed on the display screen, on the display screen in accordance with the preset scroll direction, wherein the preset scroll direction is in the array direction or in a direction reverse to the array direction.

3. The medical image observation apparatus according to claim 1, wherein the medical images are arrayed in a direction set by an operator.

4. The medical image observation apparatus according to claim 1, wherein the medical images are scrolled in a direction set by an operator.

5. The medical image observation apparatus according to claim 1, wherein the controller is further configured to remove, from a display target, a group in which a number of medical images is smaller than a predetermined number.

6. The medical image observation apparatus according to claim 1, wherein when a pointer is located within a predetermined range of the display screen, the controller starts or ends scrolling the medical images based on the instruction of an operator.

7. The medical image observation apparatus according to claim 1, wherein the controller is further configured to define a plurality of display blocks by dividing a region where the medical images are displayed on the display screen or regard the region where the medical images are displayed as one display block, and to execute control to replace, between the display blocks, medical images arrayed in the display blocks with each other.

8. The medical image observation apparatus according to claim 1, wherein the medical images are arrayed in a direction from a first end of the display screen to a second end opposing the first end or in a direction from the second end to the first end, and the arrayed medical images are scrolled in the array direction or in a direction reverse to the array direction.

9. The medical image observation apparatus according to claim 1, wherein the medical images are arrayed in a direction parallel to a direction from a lower right corner of the display screen to an upper left corner of the display screen or in a direction parallel to a direction from the upper left corner to the lower right corner, and the arrayed medical images are scrolled in the array direction or in a direction reverse to the array direction.

10. The medical image observation apparatus according to claim 1, wherein a scroll direction or a scroll rule of the medical images is set based on an instruction of an operator, the received plurality of medical images classified into the medical image groups in accordance with at least one of a type of medical image generation apparatus, an imaging condition, an image generation method, an imaging position, the instruction of the operator, a setting by the operator, and an imaging date/time, are arrayed on the display screen for each group in accordance with the set scroll direction or scroll rule, and the controller is further configured to execute control to lay out, on the display screen based on the instruction of the operator, at least one of the medical images arrayed on the display screen for each group, remove, from the display screen based on the instruction of the operator, the medical images laid out on the display screen, or lay out, on the display screen based on the instruction of the operator, at least one of the medical images arrayed on the display screen for each group and remove, from the display screen based on the instruction of the operator, the medical images laid out on the display screen.

11. The medical image observation apparatus according to claim 1, wherein the controller is further configured to execute control to replace a medical image laid out on the display screen with another medical image selected by an operator based on the instruction of the operator.

12. A medical image observation apparatus, comprising:

a display including a display screen configured to display a plurality of medical images, each of the plurality of medical images including additional information comprising examination information, identifier information of an imaged patient including an examination identifier and series identifier, and an image identifier unique to each medical image of said plurality; and a controller configured to control the display, and to execute a display control process for selecting at least one medical image to be interpreted from the plurality of medical images, wherein the controller, as part of the display control process, is further configured to execute control to:

classify the plurality of medical images into medical image groups in accordance with a predetermined condition that includes classification information from each of the plurality of medical images, said classification information comprising a type of image generator, image generation method, imaging condition, imaging position, external input, and said identifier information, display images, each of which is selected from each of the classified medical image groups, on the display screen, set, as a display block, a specific block included in a plurality of blocks to be used to set a display order of said displayed images, arrange the displayed images in the plurality of blocks in accordance with the display order, arrange display target medical images included in the plurality of medical images in the display block in accordance with the display order based on an instruction input by an operator, replace a combination of the selected images displayed on the display screen with another combination of selected images by an input scroll operation, wherein annotations comprising at least one of the additional information and the classification information are displayed with said another combination of selected images in synchronism with an elapse of a predetermined time from a stop of the input scroll operation, and replace only one of the selected images displayed on the display screen with another selected but previously undisplayed one image belonging to a same medical image group by a different input flick operation, on an image-by-image basis within the selected images of the displayed classified medical image groups, wherein on the display screen divided into a plurality of n row x m column display frames, n and m being integers of 1 or more, the medical images are arrayed in a direction obtained by repeating, from a display frame on an nth row and mth column to a display frame on a first row and first column, a procedure of arraying the medical images from the display frame on the nth row and mth column at a corner of the display screen to a display frame on an nth row and first column and subsequently arraying the medical images from a display frame on an (n−1)th row and mth column to a display frame on an (n−1)th row and first column, and the arrayed medical images are scrolled in the array direction or in a direction reverse to the array direction.

* * * * *